US006451783B1

(12) United States Patent
Hadcock et al.

(10) Patent No.: US 6,451,783 B1
(45) Date of Patent: Sep. 17, 2002

(54) TREATMENTS FOR OBESITY AND METHODS FOR IDENTIFYING COMPOUNDS USEFUL FOR TREATING OBESITY

(75) Inventors: John R. Hadcock; Andrew G. Swick, both of East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/761,320

(22) Filed: Jan. 16, 2001

Related U.S. Application Data

(60) Provisional application No. 60/176,508, filed on Jan. 18, 2000, and provisional application No. 60/206,126, filed on May 22, 2000.

(51) Int. Cl.[7] .............................................. A61K 31/33
(52) U.S. Cl. ..................................................... 514/183
(58) Field of Search .......................................... 514/183

(56) References Cited

U.S. PATENT DOCUMENTS

| | | | |
|---|---|---|---|
| 5,766,877 A | 6/1998 | Stark et al. | |
| 5,908,609 A | 6/1999 | Lee et al. | |
| 5,972,621 A | 10/1999 | Tartaglia et al. | |

FOREIGN PATENT DOCUMENTS

| | | |
|---|---|---|
| WO | WO9950295 | 10/1999 |

OTHER PUBLICATIONS

Fan et al. Nature, 1997;385:165–168.*
M. Rossi, et al., *Endocrinology*, A C–terminal fragment of Agouti–related protein increases feeding and antagonizes the effect of alpha–melanocyte stimulating hormone in vivo, vol. 139, No. 10, pp. 4428–4431.
T. Mizuno, et al., *Endocrinology*, Hypothalamic Agouti–Related Protein Messenger Ribonucleic Acid is Inhibited by Leptin and Stimulated by Fasting, vol. 140, No. 2, pp. 814–817.
J. Deyrup, *Tetrahedron Letters*, A 3+1 Cycloaddiction (1), 1971, No. 24, p. 2192–2.

* cited by examiner

*Primary Examiner*—Russell Travers
*Assistant Examiner*—San-ming Hui
(74) *Attorney, Agent, or Firm*—Peter C. Richardson; Gregg C. Benson; Todd M. Crissey

(57) ABSTRACT

The present invention provides a method of treating obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse, the method comprising the step of administering to a patent having or at risk of having one of the above-mentioned diseases a therapeutically effective amount of a compound that attenuates the binding of agouti-related protein to melanocortin receptors, but does not attenuate the binding of α-melanocyte stimulating hormone to melanocortin receptors. The present invention also provides a method of identifying a compound that is useful for the treatment or prevention of obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse, the method comprising the steps of: 1) determining if a compound affects the binding of agouti-related protein to melanocortin receptors; 2) determining if a compound affects the binding of α-melanocyte stimulating hormone to melanocortin receptors; and 3) selecting a compound that attenuates the binding of agouti-related protein to melanocortin receptors, but does not affect the binding of α-melanocyte stimulating hormone to melanocortin receptors.

3 Claims, No Drawings

TREATMENTS FOR OBESITY AND METHODS FOR IDENTIFYING COMPOUNDS USEFUL FOR TREATING OBESITY

CROSS-REFERENCE TO RELATED APPLICATION

This application claims priority of U.S. Provisional Application Nos. 60/176,508 and 60/206,126, filed Jan. 18, 2000 and May 22, 2000, respectively.

FIELD OF THE INVENTION

The present invention provides methods of treating obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse, the methods comprising the step of administering to a patient having or at risk of having one of the above-mentioned diseases or conditions a therapeutically effective amount of a compound that attenuates the binding of agouti-related protein to melanocortin receptors, but does not attenuate the binding of α-melanocyte stimulating hormone to melanocortin receptors.

The present invention also provides methods of identifying a compound that is useful for the treatment of obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse, the methods comprising the steps of: 1) determining if a compound affects the binding of agouti-related protein to melanocortin receptors; 2) determining if a compound affects the binding of α-melanocyte stimulating hormone to melanocortin receptors; and 3) selecting a compound that attenuates the binding of agouti-related protein to melanocortin receptors, but does not attenuate the binding of cc-melanocyte stimulating hormone to melanocortin receptors.

BACKGROUND OF THE INVENTION

Obesity is a devastating disease. In addition to harming physical health, obesity can wreak havoc on mental health because obesity affects self-esteem, which ultimately can affect a person's ability to interact socially with others. Unfortunately, obesity is not well understood, and societal stereotypes and presumptions regarding obesity only tend to exacerbate the psychological effects of the disease. Because of the impact of obesity on individuals and society, much effort has been expended to find ways to treat obesity, but little success has been achieved in the long-term treatment and/or prevention of obesity.

It has been discovered that overexpression of a protein called agouti-related protein (AGRP) results in obesity. Agouti-related protein has been shown to be a potent, selective, endogenous antagonist of melancortin-3 (MCR-3) and melanocortin-4 (MCR-4) receptors, which have been implicated in weight regulation. It has also been shown that ubiquitous expression of human AGRP in transgenic mice results in obesity. In contrast, α-melanocyte stimulating hormone (α-MSH) decreases feeding and is an endogenous agonist of MCR-4 and MCR-3. It is believed that the binding sites for α-MSH and AGRP on melanocortin-4 receptors are different, but may partially overlap. In one embodiment, the present invention provides a method of identifying compounds useful to treat obesity, the compounds being selected from compounds that attenuate the binding of agouti-related protein to melanocortin receptors, but do not attenuate the binding of α-melanocyte stimulating hormone to melanocortin receptors.

Sexual dysfunction occurs in males and females and includes hypoactive sexual desire disorder, sexual anhedonia and dyspareunia. Hypoactive sexual desire disorder is a disorder in which sexual fantasies and desire for sexual activity are persistently or recurrently diminished or absent, causing marked distress or interpersonal difficulties. Symptoms and signs of hypoactive sexual desire disorder include the patient complaining of a lack of interest in sex, even in ordinarily erotic situations. The disorder is usually associated with infrequent sexual activity, often causing serious conflict between partners. Sexual anhedonia is decreased or absent pleasure in sexual activity. Sexual anhedonia is almost always classified under hypoactive sexual desire disorder, because loss of pleasure typically results in loss of desire. Dyspareunia is painful coitus or attempted coitus.

Erectile dysfunction is another example of a sexual dysfunction. Erectile dysfunction, like obesity, is another condition that can result in severe emotional distress. Persons suffering from erectile dysfunction are unable to develop and/or maintain an erection of the penis. Historically, erectile dysfunction has been viewed as having biological and psychological components, and more effort appeared to be exerted on treating the psychological components of the condition. Only recently with the introduction of Viagra® have persons having this condition been offered the hope of an oral medicinal treatment. In accordance with the teachings herein, compounds that attenuate the binding of agouti-related protein to melanocortin receptors, but do not attenuate the binding of α-melanocyte stimulating hormone to melanocortin receptors are useful to treat sexual dysfunction, including erectile dysfunction.

In addition to obesity and sexual dysfunction, compounds that attenuate the binding of agouti-related protein to melanocortin receptors, but do not attenuate the binding of α-melanocyte stimulating hormone to melanocortin receptors are useful to treat diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse.

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatment of diabetes remains less than satisfactory.

The use of insulin currently requires multiple daily doses, usually by self-injection. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral hypoglycemic agents, e.g., thiazolidenediones, and, in more severe cases, insulin. However, the clinically available hypoglycemic agents can have side effects that limit their use, or an agent may not be effective with a particular patient. In the case of insulin dependent diabetes mellitus (Type I), insulin is usually the primary course of therapy. Hypoglycemic agents that have fewer side effects or succeed where others fail are needed.

Atherosclerosis, a disease of the arteries, is recognized to be a leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, give rise to development of "fibrous plaques," which consist of accumulated intimal smooth muscle cells laden with lipid and are surrounded by extra-cellular lipid, collagen, elastin and proteoglycans. The cells plus matrix form a fibrous cap that covers a deeper deposit of cell debris and more extra-cellular lipid. The lipid is primarily free and esterified cholesterol. The fibrous plaque forms slowly, and is likely in time to become calcified and necrotic, advancing to a "complicated lesion," which accounts for arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Such independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition that occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure and stroke (brain hemorrhaging). These conditions are capable of causing death in a patient. Hypertension can also contribute to the development of atherosclerosis and coronary disease. These conditions gradually weaken a patient and can lead to death.

The exact cause of essential hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus, a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure and brain hemorrhaging.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries while sodium retention increases blood volume. Thus, the lowering of insulin levels in hyperinsulinemics can prevent abnormal vascular growth and renal sodium retention caused by high insulin levels and thereby alleviate hypertension.

SUMMARY OF THE INVENTION

The present invention provides methods of treating obesity, the methods comprising the step of administering to an obese patient or a patient at risk of becoming obese a therapeutically effective amount of a compound that attenuates the binding of agouti-related protein to melanocortin receptors, but does not attenuate the binding of α-melanocyte stimulating hormone to melanocortin receptors.

The present invention also provides methods of treating obesity, the methods comprising the step of administering to an obese patient or a patient at risk of becoming obese a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

The present invention also provides methods of treating sexual dysfunction, the methods comprising the step of administering to a patient having or at risk of having sexual dysfunction a therapeutically effective amount of a compound that attenuates the binding of agouti-related protein to melanocortin receptors, but does not attenuate the binding of α-melanocyte stimulating hormone to melanocortin receptors.

The present invention also provides methods of treating sexual dysfunction, the methods comprising the step of administering to a patient having or at risk of having sexual dysfunction a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

In a preferred embodiment of the methods of treating sexual dysfunction, the sexual dysfunction is erectile dysfunction.

The present invention also provides methods of treating diabetes, the methods comprising the step of administering to a patient having or at risk of having diabetes a therapeutically effective amount of a compound that attenuates the binding of agouti-related protein to melanocortin receptors, but does not attenuate the binding of α-melanocyte stimulating hormone to melanocortin receptors.

The present invention also provides methods of treating diabetes, the methods comprising the step of administering to a patient having or at risk of having diabetes a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

In a preferred embodiment of the methods of treating diabetes, the diabetes is non-insulin dependent *diabetes mellitus*.

The present invention also provides methods of treating insulin resistance, the methods comprising the step of administering to a patient having or at risk of having insulin resistance a therapeutically effective amount of a compound that attenuates the binding of agouti-related protein to melanocortin receptors, but does not attenuate the binding of α-melanocyte stimulating hormone to melanocortin receptors.

The present invention also provides methods of treating insulin resistance, the methods comprising the step of administering to a patient having or at risk of having insulin resistance a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

The present invention also provides methods of treating hyperinsulinemia, the methods comprising the step of administering to a patient having or at risk of having hyperinsulinemia a therapeutically effective amount of a compound that attenuates the binding of agouti-related protein to melanocortin receptors, but does not attenuate the binding of α-melanocyte stimulating hormone to melanocortin receptors.

The present invention also provides methods of treating hyperinsulinemia, the methods comprising the step of administering to a patient having or at risk of having hyperinsulinemia a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

The present invention also provides methods of treating Syndrome X, the methods comprising the step of administering to a patient having or at risk of having Syndrome X a therapeutically effective amount of a compound that attenuates the binding of agouti-related protein to melanocortin receptors, but does not attenuate the binding of α-melanocyte stimulating hormone to melanocortin receptors.

The present invention also provides methods of treating Syndrome X, the methods comprising the step of administering to a patient having or at risk of having Syndrome X a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

The present invention also provides methods of treating adrenal dysfunction, the methods comprising the step of administering to a patient having or at risk of having adrenal dysfunction a therapeutically effective amount of a compound that attenuates the binding of agouti-related protein to melanocortin receptors, but does not attenuate the binding of α-melanocyte stimulating hormone to melanocortin receptors.

The present invention also provides methods of treating adrenal dysfunction, the methods comprising the step of administering to a patient having or at risk of having adrenal dysfunction a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

The present invention also provides methods of treating hypertension, the methods comprising the step of administering to a patient having or at risk of having hypertension a therapeutically effective amount of a compound that attenuates the binding of agouti-related protein to melanocortin receptors, but does not attenuate the binding of α-melanocyte stimulating hormone to melanocortin receptors.

The present invention also provides methods of treating hypertension, the methods comprising the step of administering to a patient having or at risk of having hypertension a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

The present invention also provides methods of treating hypercholesterolemia, the methods comprising the step of administering to a patient having or at risk of having hypercholesterolemia a therapeutically effective amount of a compound that attenuates the binding of agouti-related protein to melanocortin receptors, but does not attenuate the binding of α-melanocyte stimulating hormone to melanocortin receptors.

The present invention also provides methods of treating hypercholesterolemia, the methods comprising the step of administering to a patient having or a patient at risk of having hypercholesterolemia a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

The present invention also provides methods of treating atherosclerosis, the methods comprising the step of administering to a patient having or at risk of having atherosclerosis a therapeutically effective amount of a compound that attenuates the binding of agouti-related protein to melanocortin receptors, but does not attenuate the binding of α-melanocyte stimulating hormone to melanocortin receptors.

The present invention also provides methods of treating atherosclerosis, the methods comprising the step of administering to a patient having or at risk of having atherosclerosis a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

The present invention also provides methods of treating hyperlipoproteinemia, the methods comprising the step of administering to a patient having or at risk of having hyperlipoproteinemia a therapeutically effective amount of a compound that attenuates the binding of agouti-related protein to melanocortin receptors, but does not attenuate the binding of α-melanocyte stimulating hormone to melanocortin receptors.

The present invention also provides methods of treating hyperlipoproteinemia, the methods comprising the step of administering to a patient having or at risk of having hyperlipoproteinemia a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

The present invention also provides methods of treating hypertriglyceridemia, the methods comprising the step of administering to a patient having or at risk of having hypertriglyceridemia a therapeutically effective amount of a compound that attenuates the binding of agouti-related protein to melanocortin receptors, but does not attenuate the binding of α-melanocyte stimulating hormone to melanocortin receptors.

The present invention also provides methods of treating hypertriglyceridemia, the methods comprising the step of administering to a patient having or at risk of having hypertriglyceridemia a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

The present invention also provides methods of treating substance abuse, the methods comprising the step of administering to a patient abusing, having abused or at risk of abusing a substance a therapeutically effective amount of a compound that attenuates the binding of agouti-related protein to melanocortin receptors, but does not attenuate the binding of α-melanocyte stimulating hormone to melanocortin receptors.

The present invention also provides methods of treating substance abuse, the methods comprising the step of administering to a patient abusing, having abused or at risk of abusing a substance a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

In a preferred embodiment of the methods of treating substance abuse, the substance is alcohol.

In a preferred embodiment of the methods above, the melanocortin receptors are melanocortin-3 and/or 4 receptors.

In a more preferred embodiment of the methods above, the melanocortin receptors are melanocortin-4 receptors.

The present invention also provides methods of identifying a compound that is useful for the treatment of obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse, the methods comprising the steps of:
1) determining if a compound affects the binding of agouti-related protein to melanocortin receptors;
2) determining if a compound affects the binding of α-melanocyte stimulating hormone to melanocortin receptors; and
3) selecting a compound that attenuates the binding of agouti-related protein to melanocortin receptors, but does not attenuate the binding of α-melanocyte stimulating hormone to melanocortin receptors.

In a preferred embodiment of the methods of identifying a compound, the determination of whether a compound affects the binding of agouti-related protein to melanocortin receptors is accomplished using a competitive binding assay.

In a preferred embodiment of the methods of identifying a compound, the determination of whether a compound affects the binding of α-melanocyte stimulating hormone to melanocortin receptors is accomplished using a competitive binding assay.

In a more preferred embodiment of the methods of identifying a compound, the determination of whether a compound affects the binding of agouti-related protein to melanocortin receptors is accomplished using a competitive binding assay, and the determination of whether compounds affects the binding of α-melanocyte stimulating hormone to melanocortin receptors is accomplished using a competitive binding assay.

In a preferred embodiment of the methods of identifying a compound, the melanocortin receptors are melanocortin-3 and/or melanocortin-4 receptors.

In a more preferred embodiment of the methods of identifying a compound, the melanocortin receptors are melanocortin-4 receptors.

The present invention also provides pharmaceutical compositions that comprise a compound that attenuates the binding of agouti-related protein to melanocortin receptors, but does not attenuate the binding of α-melanocyte stimulating hormone to melanocortin receptors.

The present invention also provides pharmaceutical compositions that comprise 1) a compound that attenuates the binding of agouti-related protein to melanocortin receptors, but does not attenuate the binding of α-melanocyte stimulating hormone to melanocortin receptors and 2) a compound that is a melanocortin receptor agonist.

The present invention also provides pharmaceutical compositions that comprise 1) a compound that attenuates the binding of agouti-related protein to melanocortin receptors, but does not attenuate the binding of α-melanocyte stimulating hormone to melanocortin receptors, which compound is useful to treat obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse; 2) a compound that is a melanocortin receptor agonist; and 3) a second compound useful for the treatment of obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse.

The present invention also provides pharmaceutical compositions that comprise 1) a compound that attenuates the binding of agouti-related protein to melanocortin receptors, but does not attenuate the binding of α-melanocyte stimulating hormone to melanocortin receptors, which compound is useful to treat obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse; and 2) a second compound useful for the treatment of obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse.

The present invention also provides kits for the treatment of obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse, the kits comprising:

a) a first pharmaceutical composition comprising a compound that attenuates the binding of agouti-related protein to melanocortin receptors, but does not attenuate the binding of α-melanocyte stimulating hormone to melanocortin receptors;

b) a second pharmaceutical composition comprising a second compound useful for the treatment of obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse; and c) a container for the first and second compositions.

DETAILED DESCRIPTION OF THE INVENTION

The present invention provides methods of treating obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse, the methods comprising the step of administering to a patent having or at risk of having one of the above-mentioned diseases or conditions a therapeutically effective amount of a compound that attenuates the binding of agouti-related protein to melanocortin receptors, but does not attenuate the binding of α-melanocyte stimulating hormone to melanocortin receptors. Preferably, the receptors are melanocortin-3 and/or melanocortin-4 receptors. More preferably, the receptors are melanocortin-4 receptors.

The present invention also provides methods of identifying a compound that is useful for the treatment of obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse, the methods comprising the steps of: 1) determining if a compound affects the binding of agouti-related protein to melanocortin receptors; 2) determining if a compound affects the binding of α-melanocyte stimulating hormone to melanocortin receptors; and 3) selecting a compound that attenuates the binding of agouti-related protein to melanocortin receptors, but does not attenuate the binding of α-melanocyte stimulating hormone to melanocortin receptors. In a preferred embodiment of the methods, the melanocortin receptors are melanocortin-3 and/or melanocortin-4 receptors. More preferably, the receptors are melanocortin-4 receptors.

The term "therapeutically effective amount" means an amount of a compound or combination of compounds that ameliorates, attenuates, or eliminates one or more symptoms of a particular disease or condition or prevents or delays the onset of one of more symptoms of a particular disease or condition.

The term "patient" means animals, such as dogs, cats, cows, horses, sheep, geese, and humans. Particularly preferred patients are mammals, including both males and females.

The term "pharmaceutically acceptable" means that the substance or composition must be compatible with the other ingredients of a formulation, and not deleterious to the patient.

The term "attenuates" with regard to inhibition of AGRP or α-MSH binding means that the compound prevents the binding of either AGRP or α-MSH to melanocortin receptors or decreases the binding affinity of AGRP to melanocortin receptors. In the case of attenuation of AGRP binding, it is preferable if the compound being tested inhibits 25% of AGRP binding. More preferably, the compound inhibits 50%, and most preferably, greater than 75% of AGRP binding to melanocortin receptors. Similarly, with respect to α-MSH binding to melanocortin receptors, a preferred compound blocks no more than 50% of α-MSH binding. More preferably, the compound blocks no more that 25% of α-MSH binding. In a more preferred embodiment, the compound being tested blocks more than 75% of AGRP binding and blocks less than 25% of α-MSH binding. The percent inhibition of binding can be easily determined by those skilled in the art by competition and other inhibition assays in view of this disclosure. The blockade can be competitive, non-competitive, uncompetitive or a combination. In a preferred embodiment, the attenuation of binding is measured in relation to MCR-3 and/or MCR-4, and more preferably MCR-4.

The terms "reaction-inert solvent" or "inert solvent" refer to a solvent or mixture of solvents that does not interact with starting materials, reagents, intermediates or products in a manner that adversely affects the desired product.

The terms "treating", "treat" or "treatment" include preventative (e.g., prophylactic) and palliative treatment.

The phrase "compound identified by the present invention" and grammatical variations thereof means a compound that attenuates the binding of agouti-related protein to melanocortin receptors, but does not attenuate the binding of α-melanocyte stimulating hormone to melanocortin receptors, or a stereoisomer of the compound, a pharmaceutically acceptable salt of the compound, a prodrug of the compound, or a pharmaceutically acceptable salt of the prodrug. It is also contemplated that any additional pharmaceutically active compound used in combination with a compound identified by the present invention can be a stereoisomer of the additional active compound, a salt of the additional active compound, a prodrug of the additional compound or a salt of the prodrug.

The phrase "a compound that attenuates the binding of agouti-related protein to melanocortin receptors, but does not attenuate the binding of α-melanocyte stimulating hormone to melanocortin receptors" includes the stereoisomers of the compound, salts of the compound, prodrugs of the compound, and salts of the prodrugs.

The characteristics of patients at risk of having atherosclerosis are well known to those in the art and include patients who have a family history of cardiovascular disease, including hypertension and atherosclerosis, obese patients, patients who exercise infrequently, patients with hypercholesterolemia, hyperlipidemia and/or hypertriglyceridemia, patients having high levels of LDL or Lp(a), patients having low levels of HDL (hypoalphalipoproteinemia), and the like.

Patients at risk of developing diabetes include patients who have a family history of diabetes, obese patients, patients who exercise infrequently, patients who have polycystic ovary syndrome, impaired glucose tolerance or insulin resistance, and patients who have or have had gestational diabetes. The preferred type of diabetes to be treated by a compound identified by the present invention is non-insulin dependent diabetes mellitus, also known as Type II diabetes or NIDDM. It is also noted that the complications associated with diabetes such a neuropathy, retinopathy, nephropathy, cataracts, and the like, can be treated through the methods disclosed herein.

The compounds identified by the present invention can also be used to treat substance abuse. The term "substance abuse" means the socially undesirable use of a substance such as a central nervous system depressant such as alcohol; a barbiturate; ethchlorvynol; glutethimide; methaqualone; methprylon; an opioid or synthetic opioid; an anxiolytic such as alprazolam, oxazepam, temazepam, chlordiazepoxide, or diazepam; a stimulant such as amphetamine, cocaine or methamphetamine; and a hallucinogen such as LSD, marijuana, mescaline or peyote. Other examples of substances include nicotine, heroin and ecstasy. Typically, a person abusing a substance has become dependent upon the substance and has a difficult time stopping use of the substance. The most commonly abused substance is alcohol.

The compounds identified by the present invention are administered to a patient in a therapeutically effective amount. The compounds can be administered alone or as part of a pharmaceutically acceptable composition. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds identified by the present invention can be administered alone, in combination with other compounds identified by the present invention, or with other pharmaceutically active compounds. The other pharmaceutically active compounds can be intended to treat the same disease or condition as the compounds identified by the present invention or different diseases or conditions. If the patient is to receive or is receiving multiple pharmaceutically active compounds, the compounds can be administered simultaneously, or sequentially in any order. For example, in the case of tablets, the active compounds may be found in one tablet or in separate tablets, which can be administered at once or sequentially in any order. In addition, it should be recognized that the compositions may be different forms. For example, one or more compounds may be delivered via a tablet, while another is administered via injection or orally as a syrup. All combinations, delivery methods and administration sequences are contemplated.

Since one aspect of the present invention contemplates the treatment of the diseases/conditions with a combination of pharmaceutically active agents that may be administered separately, the invention further relates to combining separate pharmaceutical compositions in kit form. For example, the kit may comprise two separate pharmaceutical compositions: a compound identified by the present invention; and a second pharmaceutically active compound. The kit comprises a container for containing the separate compositions, such as a divided bottle or a divided foil packet. Additional examples of containers include syringes, boxes, bags, and the like. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of a kit is a blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and a sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of compound identified by the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter, which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds identified by the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, triglycerides, including vegetable oils such as olive oil, and injectable organic esters such as ethyl oleate. A preferred carrier is Miglyol®. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, Miglyol®, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration are preferably suppositories, which can be prepared by mixing a compound of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or compounds are admixed under sterile conditions with a physiologically acceptable carrier, and any preservatives, buffers, or propellants that may be required. Opthalmic formulations, eye ointments, powders, and solutions are also contemplated as being within the scope of this invention.

The compounds identified by the present invention may be administered to a patient at dosage levels in the range of about 0.7 to about 7,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ordinary skill in of one in the art, particularly in view of this disclosure.

The following paragraphs describe exemplary formulations, dosages etc. useful for non-human animals. The administration of a pharmaceutically active compound can be effected orally or non-orally, for example by injection. An amount of a compound of the present invention is administered such that an effective dose is received, generally a daily dose which, when administered orally to an animal is usually between 0.01 and 1000 mg/kg of body weight, preferably between 0.1 and 50 mg/kg of body weight. Conveniently, the compound can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt). Conveniently, the compound can also be added directly to the feed, as such, or in the form of an animal feed supplement, also referred to as a premix or concentrate. A premix or concentrate of the compound in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. It is important that the compound be thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of active compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Preferred medicated swine, cattle, sheep and goat feed generally contain from 1 to 400 grams of an active compound per ton of feed, the optimum amount for these animals usually being about 50 to 300 grams per ton of feed.

The preferred poultry and domestic pet feeds usually contain about 1 to 400 grams and preferably 10 to 400 grams of an active compound per ton of feed.

For parenteral administration in animals, the compounds of the present invention may be prepared in the form of a paste or a pellet and administered as an implant, usually under the skin of the head or ear of the animal.

In general, parenteral administration involves injection of a sufficient amount of a compound of the present invention to provide the animal with 0.01 to 100 mg/kg of body weight per day of the active ingredient. The preferred dosage for poultry, swine, cattle, sheep, goats and domestic pets is in the range of from 0.1 to 50 mg/kg/day.

Paste formulations can be prepared by dispersing a compound of the present invention in pharmaceutically acceptable oil such as peanut oil, sesame oil, corn oil or the like.

Pellets containing an effective amount of an active compound can be prepared by admixing the compound with a diluent such as carbowax, carnauba wax, and the like, and a lubricant, such as magnesium or calcium stearate, can be added to improve the pelleting process.

It is, of course, recognized that more than one pellet may be administered to an animal to achieve the desired dose level. Moreover, it has been found that implants may also be made periodically during the animal treatment period in order to maintain the proper active agent level in the animal's body.

The terms pharmaceutically acceptable salts or prodrugs means the salts and prodrugs of compounds that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible, of the compounds of the present invention.

The term "salts" refers to inorganic and organic salts of compounds. These salts can be prepared in situ during the final isolation and purification of a compound, or by separately reacting a purified compound in its free base form with a suitable organic or inorganic acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, besylate, esylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," *J Pharm Sci*, 66:1–19 (1977).

The term "prodrug" means compounds that are transformed in vivo to yield an active compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A. C. S. *Symposium Series*, and in *Bioreversible Carriers in Drug Design*, ed. Edward B. Roche, American Pharmaceutical Association and Pergamon Press, 1987.

For example, if an active compound contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N(alkoxycarbonyl)aminomethyl having from 3 to 9 carbon atoms, 1-(N(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound comprises an alcohol functional group, a prodrug can be formed by the replacement of the hydrogen atom of the alcohol group with a group such as $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

If a compound comprises an amine functional group, a prodrug can be formed by the replacement of a hydrogen atom in the amine group with a group such as R-carbonyl, RO-carbonyl, NRR'-carbonyl where R and R' are each independently (($C_1$–$C_{10}$)alkyl, ($C_3$–$C_7$)cycloalkyl, benzyl, or R-carbonyl is a natural α-aminoacyl or natural α-aminoacyl-natural α-aminoacyl, —C(OH)C(O)OY wherein (Y is H, ($C_1$–$C_6$)alkyl or benzyl), —C($OY_0$)$Y_1$ wherein $Y_0$ is ($C_1$–$C_4$) alkyl and $Y_1$ is (($C_1$–$C_6$)alkyl, carboxy($C_1$–$C_6$)alkyl, amino($C_1$–$C_4$)alkyl or mono-N— or di-N,N—($C_1$–$C_6$)alkylaminoalkyl, C($Y_2$)$Y_3$ wherein $Y_2$ is H or methyl and $Y_3$ is mono-N— or di-N,N—($C_1$–$C_6$) alkylamino, morpholino, piperidin-1-yl or pyrrolidin-1-yl.

The compounds identified by the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if a compound contains a double bond, both the cis and trans forms, as well as mixtures, are contemplated.

Mixtures of isomers, including stereoisomers can be separated into their individual isomers on the basis of their physical chemical differences by methods well know to those skilled in the art, such as by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, some of the compounds of this invention may be atropisomers (e.g., substituted biaryls) and are considered as part of this invention.

The compounds identified by the present invention may exist in unsolvated as well as solvated forms with pharmaceutically acceptable solvents such as water, ethanol, and the like. The present invention contemplates and encompasses both the solvated and unsolvated forms.

It is also possible that compounds identified by the present invention may exist in different tautomeric forms. All tautomers of compounds of the present invention are contemplated. For example, all of the tautomeric forms of the imidazole moiety are included in this invention. Also, for example, all keto-enol or imine-enamine forms of the compounds are included in this invention.

Those skilled in the art will recognize that compound names contained herein may be based on a particular tautomer of a compound. While the name for only a particular tautomer may be used, it is intended that all tautomers are encompassed by the name of the particular tautomer and all tautomers are considered part of the present invention.

It is also intended that the invention disclosed herein encompass compounds that are synthesized in vitro using laboratory techniques, such as those well known to synthetic chemists; or synthesized using in vivo techniques, such as through metabolism, fermentation, digestion, and the like. It is also contemplated that compounds may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found most abundantly in nature. Examples of isotopes that can be incorporated into compounds identified by the present invention include isotopes of hydrogen, carbon, nitrogen, oxygen, phosphorous, fluorine and chlorine, such as $^2H$, $^3H$, $^{13}C$, $^{14}C$, $^{15}N$ $^{18}O$, $^{17}O$, $^{31}P$, $^{32}P$, $^{35}S$, $^{18}F$, $^{135}I$ and $^{36}Cl$, respectively. Compounds identified by the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labelled compounds can generally be prepared by substituting a readily available isotopically labelled reagent for a non-isotopically labelled reagent.

An example of a compound that attenuates the binding of agouti-related protein to melanocortin receptors, particularly melanocortin-4 receptors, but does not attenuate the binding of α-melanocyte stimulating hormone to melanocortin receptors is 8,16-bis-(4-nitro-phenyl)-5,6,8,8a,13,14,16, 16a-octahydro-[1,2,4,5]tetrazino[6,1a;3,4-a']diisoquinoline, which can be synthesized in accordance with Deyrup, J. et al., *Tetrahedron Letters*, 24, 2191–2 (1971), or Grashey, R. et al., *Angew. Chem*, 74(8), 292–293 (1962).

The methods of treatment of the present invention can also include combination therapy where other pharmaceutically active agents useful for the treatment of obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, substance abuse or other diseases or conditions are used in combination with the compounds identified by the present invention that attenuate the binding of agouti-related protein to melanocortin receptors, but do not attenuate the binding of α-melanocyte stimulating hormone to melanocortin receptors. For example, compounds that attenuate the binding of agouti-related protein to melanocortin receptors, but do not attenuate the binding of α-melanocyte stimulating hormone to melanocortin receptors can be used in combination with other compounds used to treat obesity.

The additional anti-obesity agents are preferably selected from but not limited to the group consisting of a $β_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, a leptin analog, a leptin receptor agonist, a galanin antagonist, a lipase inhibitor, a bombesin agonist, a neuropeptide-Y antagonist such as NPY-1 or NPY-5, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, and a ciliary neurotrophic factor.

Especially preferred anti-obesity agents comprise those compounds selected from the group consisting of sibutramine, fenfluramine, dexfenfluramine, bromocriptine, phentermine, ephedrine, leptin, phenylpropanolamine pseudoephedrine, {4-[2-(2-[6-aminopyridin-3-yl]-2(R) hydroxyethylamino)ethoxy]phenyl}acetic acid, {4-[2-(2-[6-aminopyridin-3-yl]-2(R)hydroxylamino)ethoxy] phenyl}benzoic acid, {4-[2-(2-[6-aminopyridin-3-yl]-2(R) hydroxyethylamino)ethoxy]phenyl}propionic acid, and {4-[2-(2-[6-aminopyridin-3-yl]2(R)-hydroxyethylamino) ethoxy]phenoxy}acetic acid.

Similarly, compounds that can be used to treat sexual dysfunction, and particularly erectile dysfunction, such as Viagra® can also be used in combination with the compounds identified by the present invention.

In another aspect, the compounds identified by the present invention can be administered in combination with other compounds that are known to treat hypertension. Examples of classes of compounds that can be used to treat hypertension include calcium blockers, ACE inhibitors, diuretics, angiotensin 11 receptor blockers, β-blockers, and α-adrenergic blockers. In addition, combinations of compounds in the above-recited classes have been used to treat hypertension. Some examples of specific compounds that can be used in combination with compounds identified by the present invention include quinapril; amlodipine, including the besylate salt; nifedipine; doxazosin, including the mesylate salt; and prazosin, including the hydrochloride salt.

In one aspect, the present invention concerns the treatment of diabetes, including impaired glucose tolerance, insulin resistance, insulin dependent diabetes mellitus (Type I) and non-insulin dependent diabetes mellitus (NIDDM or Type II). Also intended to be encompassed in the treatment of diabetes are the diabetic complications, such as neuropathy, nephropathy, retinopathy or cataracts.

Diabetes can be treated by administering to a patient having diabetes (Type I or Type II), insulin resistance, impaired glucose tolerance, or any of the diabetic complications such as neuropathy, nephropathy, retinopathy or cataracts, a therapeutically effective amount of a compound identified by the present invention. It is also contemplated that diabetes be treated by administering a compound identified by the present invention along with another agent or agents that can be used to treat diabetes.

Representative agents that can be used to treat diabetes include but are not limited to insulin and insulin analogs (e.g. LysPro insulin); GLP-1 (73–7) (insulinotropin) and GLP-1 (7–36)—$NH_2$; sulfonylureas and analogs: chlorpropamide, glibenclamide, tolbutamide, tolazamide, acetohexamide, glypizide, glimepiride, repaglinide, meglitinide; biguanides: metformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, pioglitazone, englitazone, troglitazone, darglitazone, BRL49653; fatty acid oxidation inhibitors: clomoxir, etomoxir; α-glucosidase inhibitors: acarbose, miglitol, emiglitate, voglibose, MDL-25,637, camiglibose, MDL-73, 945; β-agonists: BRL 35135, BRL 37344, Ro 16-8714, ICI D7114, CL 316,243; phosphodiesterase inhibitors: L-386, 398; lipid-lowering agents: benfluorex; antiobesity agents: fenfluramine and orlistat; vanadate and vanadium complexes (e.g. Naglivan®) and peroxovanadium complexes; amylin antagonists; glucagon antagonists; gluconeogenesis inhibitors; somatostatin analogs; antilipolytic agents: nicotinic acid, acipimox, WAG 994; and glycogen phosphorylase inhibitors, such as those disclosed in WO 96/39385 and WO 96/39384. Also contemplated in combination with compounds of the present invention are pramlintide acetate (Symlin™) and nateglinide. Any agent or combination of agents can be administered as described above.

In addition, the compounds identified by the present invention can be administered in combination with other pharmaceutical agents such as cholesterol biosynthesis inhibitors and cholesterol absorption inhibitors, especially HMG-CoA reductase inhibitors and HMG-CoA synthase inhibitors, HMG-CoA reductase and synthase gene expression inhibitors, CETP inhibitors, biles acid sequesterants, fibrates, ACAT inhibitors, squalene synthetase inhibitors, anti-oxidants and niacin. The compounds identified by the present invention may also be administered in combination with naturally occurring compounds that act to lower plasma cholesterol levels. These naturally occurring compounds are commonly called nutraceuticals and include, for example, garlic extract, Benecol®, and niacin.

Specific cholesterol absorption inhibitors and cholesterol biosynthesis inhibitors are described in detail below. Additional cholesterol absorption inhibitors are known to those skilled in the art and are described, for example, in WO 94/00480.

Any HMG-CoA reductase inhibitor may be employed as an additional compound in the combination therapy aspect of the present invention. The term HMG-CoA reductase inhibitor refers to a compound that inhibits the biotransformation of hydroxymethylglutaryl-coenzyme A to mevalonic acid as catalyzed by the enzyme HMG-CoA reductase. Such inhibition may be determined readily by one of skill in the art according to standard assays (e.g., *Methods of Enzymology*, 71: 455–509 (1981); and the references cited therein). A variety of these compounds are described and referenced below. U.S. Pat. No. 4,231,938 discloses certain compounds isolated after cultivation of a microorganism belonging to the genus Aspergillus, such as lovastatin. Also, U.S. Pat. No. 4,444,784 discloses synthetic derivatives of the aforementioned compounds, such as simvastatin. Additionally, U.S. Pat. No. 4,739,073 discloses certain substituted indoles, such as fluvastatin. Further, U.S. Pat. No. 4,346,227 discloses ML-236B derivatives, such as pravastatin. In addition, EP 491,226 teaches certain pyridyldihydroxyheptenoic acids, such as rivastatin. Also, U.S. Pat. No. 4,647,576 discloses certain 6-[2-(substituted-pyrrol-1-yl)-alkyl]-pyran-2-ones such as atorvastatin. Other HMG-CoA reductase inhibitors will be known to those skilled in the art. Examples of marketed products containing HMG-CoA reductase inhibitors that can be used in combination with compounds of the present invention include Baycol®, Lescol®, Lipitor®, Mevacor®, Pravachol® and Zocor®.

Any HMG-CoA synthase inhibitor may be used as the second compound in the combination therapy aspect of this invention. The term HMG-CoA synthase inhibitor refers to a compound which inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art according to standard assays (e.g., *Methods of Enzymology*, 35: 155–160 (1975); and *Methods of Enzymology*, 110: 19–26 (1985); and the references cited therein). A variety of these compounds are described and referenced below. U.S. Pat. No. 5,120,729 discloses certain beta-lactam derivatives. U.S. Pat. No. 5,064,856 discloses certain spiro-lactone derivatives prepared by culturing the microorganism MF5253. U.S. Pat. No. 4,847,271 discloses certain oxetane compounds such as 11-(3-hydroxymethyl-4-oxo-2-oxetayl)-3,5,7-trimethyl-2,4-undecadienoic acid derivatives. Other HMG-CoA synthase inhibitors will be known to those skilled in the art.

Any compound that decreases HMG-CoA reductase gene expression may be used as an additional compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities. Such regulation is readily determined by those skilled in the art according to standard assays (*Methods of Enzymology,* 110: 9–19 1985). Several such compounds are described and referenced below however other inhibitors of HMG-CoA reductase gene expression will be known to those skilled in the art. U.S. Pat. No. 5,041,432 discloses certain 15-substituted lanosterol derivatives. Other oxygenated sterols that suppress the biosynthesis of HMG-CoA reductase are discussed by E. I. Mercer (*Prog. Lip. Res.,* 32:357–416 1993).

Any compound having activity as a CETP inhibitor can serve as the second compound in the combination therapy aspect of the instant invention. The term CETP inhibitor refers to compounds that inhibit the cholesteryl ester transfer protein (CETP) mediated transport of various cholesteryl esters and triglycerides from HDL to LDL and VLDL. A variety of these compounds are described and referenced below however other CETP inhibitors will be known to those skilled in the art. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.,* 49(8): 815–816 (1996), and *Bioorg. Med. Chem. Lett.;* 6:1951–1954 (1996), respectively. Other CETP inhibitors that can be used in combination with compounds identified by the present invention are disclosed in WO 99/20302, EP 796846, EP818197, EP 818448, WO 99/14204, WO 99/41237, WO 95/04755, WO 96/15141, WO 96/05227, DE 19704244, DE19741051, DE 19741399, DE 19704243, DE 19709125, DE 19627430, DE 19832159, DE 19741400, JP 11049743, and JP 09059155. Preferred CETP inhibitors that can be used in combination with the compounds identified by the present invention include:

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-acid propyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid propyl ester;

[2S,4S]4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;

[2S,4S]2-cyclopropyl-4-[(3,5-dichloro-benzyl)-methoxycarbonyl-amino]-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid propyl ester.

Any ACAT inhibitor can serve as an additional compound in the combination therapy aspect of this invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research.,* 24:1127 (1983). A variety of these compounds are described and referenced below; however, other ACAT inhibitors will be known to those skilled in the art. U.S. Pat. No. 5,510,379 discloses certain carboxysulfonates, while WO 96/26948 and WO 96/10559 both disclose urea derivatives having ACAT inhibitory activity.

Any compound having activity as a squalene synthetase inhibitor can serve as an additional compound in the combination therapy aspect of the instant invention. The term squalene synthetase inhibitor refers to compounds that inhibit the condensation of two molecules of farnesylpyrophosphate to form squalene, a reaction that is catalyzed by the enzyme squalene synthetase. Such inhibition is readily determined by those skilled in the art according to standard methodology (*Methods of Enzymology*, 15:393–454 (1969); and *Methods of Enzymology*, 110: 359–373 (1985); and references cited therein). A summary of squalene synthetase inhibitors has been complied in *Curr. Op. Ther. Patents*, 861–4, (1993). European patent application publication Number 0 567 026 A1 discloses certain 4,1-benzoxazepine derivatives as squalene synthetase inhibitors and their use in the treatment of hypercholesterolemia and as fungicides. European patent application publication Number 0 645 378 A1 discloses certain seven- or eight-membered heterocycles as squalene synthetase inhibitors and their use in the treatment and prevention of hypercholesterolemia and fungal infections. European patent application publication Number 0 645 377 A1 discloses certain benzoxazepine derivatives as squalene synthetase inhibitors useful for the treatment of hypercholesterolemia or coronary sclerosis. European patent application publication Number 0 611 749 A1 discloses certain substituted amic acid derivatives useful for the treatment of arteriosclerosis. European patent application publication Number 0 705 607 A2 discloses certain condensed seven- or eight-membered heterocyclic compounds useful as antihypertriglyceridemic agents. PCT publication WO 96/09827 discloses certain combinations of cholesterol absorption inhibitors and cholesterol biosynthesis inhibitors including benzoxazepine derivatives and benzothiazepine derivatives. European patent application publication Number 0 701 725 A1 discloses a process for preparing certain optically-active compounds, including benzoxazepine derivatives, having plasma cholesterol and triglyceride lowering activities. Other compounds that are marketed for hyperlipidemia, including hypercholesterolemia and which are intended to help prevent or treat atherosclerosis include bile acid sequestrants, such as Colestid®, LoCholest® and Questran®; and fibric acid derivatives, such as Atromid®, Lopid® and Tricor®. These compounds can also be used in combination with a compound identified by the present invention.

It is also contemplated that the compounds of the present invention be administered with a lipase inhibitor and/or a glucosidase inhibitor, which are typically used in the treatment of conditions resulting from the presence of excess triglycerides, free fatty acids, cholesterol, cholesterol esters or glucose including, interalia, obesity, hyperlipidemia, hyperlipoproteinemia, Syndrome X, and the like.

In a combination with a compound identified by the present invention, any lipase inhibitor or glucosidase inhibitor may be employed. Preferred lipase inhibitors comprise gastric or pancreatic lipase inhibitors such as orlistat. Preferred glucosidase inhibitors comprise amylase inhibitors.

A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Accordingly, compounds, including lipase inhibitors that selectively limit or inhibit the absorption of ingested fat precursors are useful in the treatment of conditions including obesity, hyperlipidemia, hyperlipoproteinemia, Syndrome X, and the like.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions.

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology*, 92, 125 (1987).

A variety of lipase inhibitors are known to one of ordinary skill in the art. However, in the practice of the methods, pharmaceutical compositions and kits of the instant invention, generally preferred lipase inhibitors are those inhibitors that are selected from the group consisting of lipstatin, tetrahydrolipstatin (orlistat), FL-386, WAY-121898, Bay-N-3176, valilactone, esterastin, ebelactone A, ebelactone B and RHC 80267.

The pancreatic lipase inhibitors lipstatin, 2S, 3S, 5S, 7Z, 10Z)-5-[(S)-2-formamido-4-methyl-valeryloxy]-2-hexyl-3-hydroxy-7,10-hexadecanoic acid lactone, and tetrahydrolipstatin (orlistat), 2S, 3S, 5S)-5-[(S)-2-formamido-4-methyl-valeryloxy]2-hexyl-3-hydroxy-hexadecanoic acid lactone, and the variously substituted N-formylleucine derivatives and stereoisomers thereof, are disclosed in U.S. Pat. No. 4,598,089.

The pancreatic lipase inhibitor FL-386, 1-[4-(2-methylpropyl)cyclohexyl]-2[(phenylsulfonyl)oxy]-ethanone, and the variously substituted sulfonate derivatives related thereto, are disclosed in U.S. Pat. No. 4,452,813.

The pancreatic lipase inhibitor WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151.

The lipase inhibitor Bay-N-3176, N-3-trifluoromethylphenyl-N'-3-chloro-4'-trifluoromethylphenylurea, and the various urea derivatives related thereto, are disclosed in U.S. Pat. No. 4,405,644.

The pancreatic lipase inhibitor valilactone, and a process for the preparation thereof by the microbial cultivation of Actinomycetes strain MG147-CF2, are disclosed in Kitahara, et al., *J. Antibiotics*, 40 (11), 1647–1650 (1987).

The lipase inhibitor esteracin, and certain processes for the preparation thereof by the microbial cultivation of Streptomyces strain ATCC 31336, are disclosed in U.S. Pat. Nos. 4,189,438 and 4,242,453.

The pancreatic lipase inhibitors ebelactone A and ebelactone B, and a process for the preparation thereof by the microbial cultivation of Actinomycetes strain MG7-G1, are disclosed in Umezawa, et al., *J. Antibiotics*, 33, 1594–1596 (1980). The use of ebelactones A and B in the suppression of monoglyceride formation is disclosed in Japanese Kokai 08-143457, published Jun. 4, 1996.

The lipase inhibitor RHC 80267, cyclo-O,O'-[(1,6-hexanediyl)-bis(iminocarbonyl)]dioxime, and the various bis(iminocarbonyl)dioximes related thereto may be prepared as described in Petersen et al., *Liebig's Annalen*, 562, 205–229 (1949). The ability of RHC 80267 to inhibit the activity of myocardial lipoprotein lipase is disclosed in Carroll et al., *Lipids*, 27, pp. 305–307 (1992) and Chuang et al., *J. Mol. Cell Cardiol.*, 22, 1009–1016 (1990).

A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that both hypoglycemias and chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom.

In combination with a compound identified by the present invention, any glucosidase inhibitor may be employed, however, a generally preferred glucosidase inhibitor comprises an amylase inhibitor. An amylase inhibitor is a glucosidase inhibitor that inhibits the enzymatic degradation of starch or glycogen into maltose. The inhibition of such enzymatic degradation is beneficial in reducing amounts of bioavailable sugars, including glucose and maltose, and the concomitant deleterious conditions resulting therefrom.

A variety of glucosidase and amylase inhibitors are known to one of ordinary skill in the art. However, in the practice of the methods and pharmaceutical compositions of the instant invention, generally preferred glucosidase inhibitors are those inhibitors that are selected from the group consisting of acarbose, adiposine, voglibose, miglitol, emiglitate, MDL-25637, camiglibose, tendamistate, Al-3688, trestatin, pradimicin-Q and salbostatin.

The glucosidase inhibitor acarbose, O-4,6-dideoxy-4-[[(1S,4R,5S,6S)-4,5,6-trihydroxy-3-(hydroxymethyl)-2-cyclohexen-1-yl]amino]-α-glucopyranosyl-(1→4)-O-α-D-glucopyranosyl-(1→40-D-glucose, the various amino sugar derivatives related thereto and a process for the preparation thereof by the microbial cultivation of Actinoplanes strains SE 50 (CBS 961.70), SB 18(CBS 957.70), SE 82 (CBS 615.71), SE 50/13 (614.71) and SE 50/110 (674.73) are disclosed in U.S. Pat. Nos. 4,062,950 and 4,174,439 respectively.

The glucosidase inhibitor adiposine, consisting of adiposine forms 1 and 2, is disclosed in U.S. Pat. No. 4,254,256. Additionally, a process for the preparation and purification of adiposine is disclosed in Namiki et al., *J. Antiobiotics*, 35, 1234–1236 (1982).

The glucosidase inhibitor voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559.

The glucosidase inhibitor miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436.

The glucosidase inhibitor emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772.

The glucosidase inhibitor MDL-25637, 2,6-dideoxy-7-O-p-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765.

The glucosidase inhibitor camiglibose, methyl 6-deoxy-6-[(2R,3R,4R,5S)-3,4,5-trihydroxy-2-(hydromethyl) piperidino]α-D-glucopyranoside sesquihydrate, the deoxynojirimycin derivatives related thereto, the various pharmaceutically acceptable salts thereof and synthetic methods for the preparation thereof, are disclosed in U.S. Pat. Nos. 5,157,116 and 5,504,078.

The amylase inhibitor tendamistat, the various cyclic peptides related thereto and processes for the preparation thereof by the microbial cultivation of *Streptomyces tendae* strains 4158 or HAG 1226, are disclosed in U.S. Pat. No. 4,451,455.

The amylase inhibitor Al-3688, the various cyclic polypeptides related thereto, and a process for the preparation thereof by the microbial cultivation of *Streptomyces aureofaciens* strain FH 1656, are disclosed in U.S. Pat. No. 4,623,714.

The amylase inhibitor trestatin, consisting of a mixture of trestatin A, trestatin B and trestatin C, the various trehalose-containing aminosugars related thereto and a process for the preparation thereof by the microbial cultivation of *Streptomyces dimorphogenes* strains NR-320-OM7HB and NR-320-OM7HBS, are disclosed in U.S. Pat. No. 4,273,765.

The glucosidase inhibitor pradimicin-Q and a process for the preparation thereof by the microbial cultivation of *Actinomadura verrucospora* strains R103-3 or A10102, are disclosed in U.S. Pat. Nos. 5,091,418 and 5,217,877 respectively.

The glycosidase inhibitor salbostatin, the various pseudosaccharides related thereto, the various pharmaceutically acceptable salts thereof and a process for the preparation thereof by the microbial cultivation of *Streptomyces albus* strain ATCC 21838, are disclosed in U.S. Pat. No. 5,091,524.

Preferred lipase inhibitors comprise compounds selected from the group consisting of lipstatin, tetrahydrolipstatin, FL-386, WAY-121898, Bay-n-3176, valilactone, esteracin, ebelactone A, ebelactone B, RHC 80267, stereoisomers thereof, and pharmaceutically acceptable salts of said compounds and stereoisomers. The compound tetrahydrolipstatin is especially preferred.

Preferred glucosidase inhibitors comprise compounds selected from the group consisting of acarbose, adiposine, voglibose, miglitol, emiglitate, MDL-25637, camiglibose, pradimicin-Q, and salbostatin. An especially preferred glucosidase inhibitor is acarbose. Especially preferred glucosidase inhibitors further comprise amylase inhibitors that are selected from the group consisting of tendamistate, Al-3688 and trestatin.

In addition, the present invention includes the use of compounds identified by the present invention in combination with apo B secretion/MTP inhibitors.

A variety of apo B secretion/MTP inhibitors are known to one of ordinary skill in the art. Although any apo B secretion/MTP inhibitor may be used in the practice of the methods and pharmaceutical compositions of the instant invention, generally preferred apo B secretion/MTP inhibitors include those compounds that are disclosed in, for example, European Patent Application Publication Numbers EP 643057, EP 719763, EP 753517, EP 764647, EP 765878, EP 779276, EP 779279, EP 799828, EP 799829, EP 802186, EP 802188, EP 802192, and EP 802197; PCT Application Publication Numbers WO 96/13499, WO 96/33193, WO 96/40640, WO 97/26240, WO 97/4325, WO 97/43257, WO 98/16526 and WO 98/23593; and U.S. Pat. Nos. 5,595,872; 5,646,162; 5,684,014; 5,712,279; 5,739,135 and 5,789,197.

Especially preferred apo-B secretion/MTP inhibitors are those biphenyl-2-carboxylic acid-tetrahydroisoquinolin-6-yl amide derivatives disclosed in PCT Application Publication Numbers WO 96/40640 and WO 98/23593. Especially preferred apo B secretion/MTP inhibitors disclosed in PCT Application Publication Numbers WO 96/40640 and WO 98/23593, and useful in the methods and pharmaceutical compositions of the present invention, are 4'-trifluoromethyl-biphenyl-2-carboxylic acid-[2-(1H-[1,2,4]triazol-3-ylmethyl)-1,2,3,4-tetrahydroisoquin-6-yl]amide and 4'-trifluoromethyl-biphenyl-2-carboxylic acid-[2-(acetylaminoethyl)-1,2,3,4-tetrahydroisoquinolin-6-yl]-amide.

Another especially preferred class of apo B secretion/MTP inhibitors is disclosed in U.S. Pat. Nos. 5,595,872; 5,721,279; 5,739,135 and 5,789,197.

Especially preferred apo B secretion/MTP inhibitors disclosed in U.S. Pat. Nos. 5,595,872; 5,721,279; 5,739,135 and 5,789,197 and useful in the methods and pharmaceutical compositions of the present invention, are 9-(4-{4-[4'-trifluoromethyl-biphenyl-2-carbonyl)-amino]-piperidin-1-yl}-butyl-9H-fluorene-9-carboxylic acid-(2,2,2-trifluoroethyl)-amide and 9-{4-[4-(2-benzothiazol-2-ylbenzoylamino)-piperidin-1-yl]-butyl}-9H-fluorene-9-carboxylic acid-(2,2,2-trifluoroethyl)-amide.

Another class of especially preferred apo B secretion/MTP inhibitors is disclosed in PCT Application Publication Number WO 98/16526.

Especially preferred apo B secretion/MTP inhibitors disclosed in PCT Application Publication Number WO 98/16526, and useful in the methods and pharmaceutical compositions of the present invention, are [11a-R]-8-[-(4-cyanophenyl)methoxy]-2-cyclopentyl-7-(prop-2-enyl)-2,3,11,11a-tetrahydro-6H-pyrazino[1,2b]isoquinoline-1,4-dione and [11a-R]-cyclopentyl-7-(prop-2-enyl)-8-[(pyridin-2-yl)methoxy]11,11a-tetrahydro-6H-pyrazino[1,2b]isoquinoline-1,4-dione.

Another especially preferred class of apo B secretion/MTP inhibitors is disclosed in U.S. Pat. No. 5,684,014.

An especially preferred apo B secretion/MTP inhibitor disclosed in U.S. Pat. No. 5,684,014, and useful in the methods and pharmaceutical compositions of the present invention, is 2-cyclopentyl-2-[4-(2,4-dimethyl-pyrido[2,3-b]indol-9-ylmethyl)-phenyl]-N-(2-hydroxy-1-phenyl-ethyl)-acetamide.

Yet another class of especially preferred apo B secretion/MTP inhibitors is disclosed in U.S. Pat. No. 5,646,162.

An especially preferred apo B secretion/MTP inhibitor disclosed in U.S. Pat. No. 5,646,162 and useful in the methods and pharmaceutical compositions of the present invention, is 2-cyclopentyl-N-(2-hydroxy-1-phenylethyl)-2-[4-(quinolin-2ylmethoxy)-phenyl]-acetamide.

Additional apo B secretion/MTP inhibitors that can be used in combination with compounds identified by the present invention are disclosed in U.S. provisional patent application No. 60/164,803, filed Nov. 11, 1999. Examples of specific preferred apo B secretion/MTP inhibitors disclosed in this application include:

7-amino-quinoline-3-carboxylic acid ethyl ester;
7-[(4'-trifluoromethyl-biphenyl-2-carbonyl)-amino]-quinoline-3-carboxylic acid ethyl ester;
7-[(4'-trifluoromethyl-biphenyl-2-carbonyl)-amino]-quinoline-3-carboxylic acid;
7-[(4'-trifluoromethyl-biphenyl-2-carbonyl)-amino]-quinoline-3-carboxylic acid (dipyridin-2-yl-methyl)-amide;
7-[(4'-trifluoromethyl-biphenyl-2-carbonyl)-amino]-quinoline-3-carboxylic acid (dipyridin-2-yl-methyl)-amide, ethanesulfonate;
7-[(4'-trifluoromethyl-biphenyl-2-carbonyl)-amino]-quinoline-3-carboxylic acid (dipyridin-2-yl-methyl)-amide, bis-ethanesulfonate;
7-[(4'-trifluoromethyl-biphenyl-2-carbonyl)-amino]-quinoline-3-carboxylic acid (phenylpyridin-2-yl-methyl)-amide;
7-[(4'-trifluoromethyl-biphenyl-2-carbonyl)-amino]-quinoline-3-carboxylic acid (phenylpyridin-2-yl-methyl)-amide, ethanesulfonate;
(S)-7-[(4'-trifluoromethyl-biphenyl-2-carbonyl)-amino]-quinoline-3-carboxylic acid (phenyl-pyridin-2-yl-methyl)-amide;
(S)-7-[(4'-trifluoromethyl-biphenyl-2-carbonyl)-amino]-quinoline-3-carboxylic acid (phenyl-pyridin-2-yl-methyl)-amide, ethanesulfonate;
(S)-7-[(4'-trifluoromethyl-biphenyl-2-carbonyl)-amino]-quinoline-3-carboxylic acid (phenyl-pyridin-2-yl-methyl)-amide, bis-ethanesulfonate;
(R)-7-[(4'-trifluoromethyl-biphenyl-2-carbonyl)-amino]-quinoline-3-carboxylic acid (phenyl-pyridin-2-yl-methyl)-amide;
(R)-7-[(4'-trifluoromethyl-biphenyl-2-carbonyl)-amino]-quinoline-3-carboxylic acid (phenyl-pyridin-2-yl-methyl)-amide, ethanesulfonate;
7-[(4'-trifluoromethyl-biphenyl-2-carbonyl)-amino]-quinoline-3-carboxylic acid (phenylpyridin-2-yl-methyl)-amide, bis-ethanesulfonate;
7-[(4'-trifluoromethyl-biphenyl-2-carbonyl)-amino]-quinoline-3-carboxylic acid (1-carbamoyl-2-phenyl-ethyl)-amide;
7-[(4'-trifluoromethyl-biphenyl-2-carbonyl)-amino]-quinoline-3-carboxylic acid (carbamoyl-phenyl-methyl)-amide;
7-[(4'-trifluoromethyl-biphenyl-2-carbonyl)-amino]-quinoline-3-carboxylic acid propylamide;
7-[(4'-trifluoromethyl-biphenyl-2-carbonyl)-amino]-quinoline-3-carboxylic acid (2,2,2-trifluoro-ethyl)-amide;
7-[(4'-trifluoromethyl-biphenyl-2-carbonyl)-amino]-quinoline-3-carboxylic acid (1-methyl-1-phenyl-ethyl)-amide;
7-[(4'-trifluoromethyl-biphenyl-2-carbonyl)-amino]-quinoline-3-carboxylic acid cyclopentylamide;
7-[(4'-trifluoromethyl-biphenyl-2-carbonyl)-amino]-quinoline-3-carboxylic acid (1-phenyl-propyl)-amide;
(R)-7-[(4'-trifluoromethyl-biphenyl-2-carbonyl)-amino]-quinoline-3-carboxylic acid (1-phenyl-ethyl)-amide, ethanesulfonate;
7-[(4'-trifluoromethyl-biphenyl-2-carbonyl)-amino]-quinoline-3-carboxylic acid (1-phenyl-ethyl)-amide;
7-[(4'-trifluoromethyl-biphenyl-2-carbonyl)-amino]-quinoline-3-carboxylic acid (1-pyridin-2-yl-propyl)-amide;

(R)-7-[(4'-trifluoromethyl-biphenyl-2-carbonyl)-amino]-quinoline-3-carboxylic acid (1-pyridin-2-yl-propyl)-amide;

(R)-7-[(4'-trifluoromethyl-biphenyl2-carbonyl)-amino]-quinoline-3-carboxylic acid (1-pyridin-2-yl-propyl)-amide, ethanesulfonate;

(S)-7-[(4'-trifluoromethyl-biphenyl-2-carbonyl)-amino]-quinoline-3-carboxylic acid (1-pyridin-2-yl-propyl)-amide;

(S)-7-[(4'-trifluoromethyl-biphenyl-2-carbonyl)-amino]-quinoline-3-carboxylic acid (1-pyridin-2-yl-propyl)-amide ethanesulfonate;

7-[(4'-trifluoromethyl-biphenyl-2-carbonyl)-amino]-quinoline-3-carboxylic acid (1-pyridin-2-yl-propyl)-amide, ethanesulfonate;

7-[(4'-trifluoromethyl-biphenyl-2-carbonyl)-amino]-quinoline-3-carboxylic acid (pyridin-2-ylmethyl)-amide, ethanesulfonate;

7-[(4'-trifluoromethyl-biphenyl-2-carbonyl)-amino]-quinoline-3-carboxylic acid (2-pyridin-2-yl-ethyl)-amide, ethanesulfonate;

7-[(4'-trifluoromethyl-biphenyl-2-carbonyl)-amino]-quinoline-3-carboxylic acid ethylamide, ethanesulfonate;

7-[(4'-trifluoromethyl-biphenyl-2-carbonyl)-amino]-quinoline-3-carboxylic acid butylamide, ethanesulfonate;

7-[(4'-trifluoromethyl-biphenyl2-carbonyl)-amino]-quinoline-3-carboxylic acid (thiophen-2-ylmethyl)-amide, ethanesulfonate;

7-[(4'-trifluoromethyl-biphenyl-2-carbonyl)-amino]-quinoline-3-carboxylic acid (1-methyl-1-pyridin-2-yl-ethyl)-amide;

(S)-7-[(4'-trifluoromethyl-biphenyl-2-carbonyl)-amino]-quinoline-3-carboxylic acid (1-pyridin-2-yl-ethyl)-amide;

(R)-7-[(4'-trifluoromethyl-biphenyl-2-carbonyl)-amino]-quinoline-3-carboxylic acid (1-pyridin-2-yl-ethyl)-amide ethanesulfonate;

7-[(4'-trifluoromethyl-biphenyl-2-carbonyl)-amino]-quinoline-3-carboxylic acid (1-pyridin-2-yl-ethyl)-amide;

7-[(4'-trifluoromethyl-biphenyl-2-carbonyl)-amino]-quinoline-3-carboxylic acid (1-pyridin-2-yl-ethyl)-amide ethanesulfonate;

7-[(4'-trifluoromethyl-biphenyl-2-carbonyl)-amino]-quinoline-3-carboxylic acid amide;

7-[(4'-trifluoromethyl-biphenyl-2-carbonyl)-amino]-quinoline-3-carboxylic acid benzylamide;

7-[(4'-trifluoromethyl-biphenyl-2-carbonyl)-amino]-quinoline-3-carboxylic acid 4-methoxy-benzylamide;

7-[(4'-trifluoromethyl-biphenyl-2-carbonyl)-amino]-quinoline-3-carboxylic acid 4-chlorobenzylamide;

7-[(4'-trifluoromethyl-biphenyl-2-carbonyl)-amino]-quinoline-3-carboxylic acid 4-methyl-benzylamide;

7-[(4'-trifluoromethyl-biphenyl-2-carbonyl)-amino]-quinoline-3-carboxylic acid cyclopropylmethyl-amide;

7-[(4'-trifluoromethyl-biphenyl-2-carbonyl)-amino]-quinoline-3-carboxylic acid 4-fluorobenzylamide;

7-[(4'-trifluoromethyl-biphenyl-2-carbonyl)-amino]-quinoline-3-carboxylic acid isopropyl-amide;

7-[(4'-trifluoromethyl-biphenyl-2-carbonyl)-amino]-quinoline-3-carboxylic acid benzhydryl-amide;

7-[(4'-trifluoromethyl-biphenyl-2-carbonyl)-amino]-quinoline-3-carboxylic acid cyclopropylamide;

7-[(4'-trifluoromethyl-biphenyl-2-carbonyl)-amino]-quinoline-3-carboxylic acid [1-(4-fluoro-phenyl)-ethyl]-amide;

7-[(4'-trifluoromethyl-biphenyl-2-carbonyl)-amino]-quinoline-3-carboxylic acid 3-methyl-benzylamide;

7-[(4'-trifluoromethyl-biphenyl-2-carbonyl)-amino]-quinoline-3-carboxylic acid 3-methoxy-benzylamide;

7-[(4'-trifluoromethyl-biphenyl-2-carbonyl)-amino]-quinoline-3-carboxylic acid 3-chlorobenzylamide;

7-[(4'-trifluoromethyl-biphenyl-2-carbonyl)-amino]-quinoline-3-carboxylic acid 2-fluorobenzylamide;

7-[(4'-trifluoromethyl-biphenyl-2-carbonyl)-amino]-quinoline-3-carboxylic acid 3-fluoro-benzylamide;

7-[(4'-trifluoromethyl-biphenyl-2-carbonyl)-amino]-quinoline-3-carboxylic acid 2-methyl-benzylamide;

7-[(4'-trifluoromethyl-biphenyl-2-carbonyl)-amino]-quinoline-3-carboxylic acid 2-methoxy-benzylamide;

7-[(4'-trifluoromethyl-biphenyl-2-carbonyl)-amino]-quinoline-3-carboxylic acid 2-chlorobenzylamide;

4'-trifluoromethyl-biphenyl-2-carboxylic acid [3-(pyrrolidine-1-carbonyl)-quinolin-7-yl]amide;

4'-trifluoromethyl-biphenyl-2-carboxylic acid [3-(morpholine-4-carbonyl)-quinolin-7-yl]amide;

7-[(4'-trifluoromethyl-biphenyl-2-carbonyl)-amino]-quinoline-3-carboxylic acid diethylamide; and 4'-trifluoromethyl-biphenyl-2-carboxylic acid [3-(piperidine-1-carbonyl)quinolin-7-yl]-amide.

In another embodiment, the present invention provides a method of treating obesity, sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse, the method comprising the step of administering to an obese patient, a patient at risk of becoming obese, or a patient having or at risk of having sexual dysfunction (including erectile dysfunction), diabetes, insulin resistance, hyperinsulinemia, Syndrome X, adrenal dysfunction, hypertension, hypercholesterolemia, atherosclerosis, hyperlipoproteinemia, hypertriglyceridemia, or substance abuse a therapeutically effective amount of a compound that attenuates the binding of agouti-related protein to melanocortin receptors, but does not attenuate the binding of α-melanocyte stimulating hormone to melanocortin receptors in combination with a compound that is a melanocortin receptor agonist.

Particularly preferred melanocortin receptor agonists are melanocortin-4 receptor agonists. Examples of melanocortin-4 receptor agonists include melanotan II (MT II), α-MSH and NDP-MSH.

All documents cited in this patent application are hereby incorporated by reference.

The examples presented below are intended to illustrate particular embodiments of the invention, and are not intended to limit the scope of the specification, including the claims, in any manner.

EXAMPLES

In order to identify compounds that attenuate the binding of AGRP to melanocortin receptors, particularly melanocortin 3 and/or 4 receptors, but do not attenuate the binding of α-MSH to melanocortin receptors, a series of two radioligand binding assays can be used. The first radioligand binding assay is an [$^{125}$I]AGRP competition binding assay. Compounds that attenuate binding of [$^{125}$I]AGRP or AGRP would be detected in this assay. It is noted that compounds can attenuate the binding of AGRP to melanocortin 3 and/or 4 receptors by binding to melanocortin 3 and/or 4 receptors or by binding to AGRP itself. The second radioligand binding assay is an assay using radiolabeled melanocortin ligands, for example, [$^{125}$I]norleucine D-phenylalanine melanocyte stimulating hormone ([$^{125}$I]NDP-MSH). Membranes prepared from cells expressing either melanocortin 3 or 4 receptors are used in the radioligand binding assays. The preparation and use of [$^{125}$I]AGRP and [$^{125}$I]NDP-MSH is well known in the art. See, for example, Dang et al., *Molecular Endocrinology*, 13, 148–155 (1999). In addition, the preparation and use of membranes from cells expressing either melanocortin 3 or 4 receptors are also well known in the art. See, Bass, et al., *Molecular Pharmacology*, 50, 709–715 (1996).

Radioligand Binding Assays
$^{125}$I AGRP Competition Binding Assay

Specific Activity of [$^{125}$I]AGRP is 2200 Ci/mmole. The final concentration of [$^{125}$I]AGRP is 100 pM. Therefore, a 2 nM (20×) stock needs to be made in binding buffer. The concentration of [$^{125}$I]AGRP varies from 40–60 nM. [$^{125}$I]AGRP can be obtained from New England Nuclear, Boston, Mass.

The competition assay can be run using 96 well plates. The last row (Row H) in the 96 well plate should be for total ("totals") counts per minute (cpm) bound (H1,2), 1 μM AGRP (H3,4), 1 μM NDP-MSH (H5,6) and filter blanks (just binding buffer buffer, no membranes; H7,8). The other rows (A–G) should be for compounds to be tested. Up to seven compounds can be tested in 7 point competition curves in a 96 well format. The first six rows for each compound can be used for testing 6 compounds at 6 concentrations in duplicate. An example for a single compound is outlined below. The next compound would be in rows A–F, columns 3 and 4. A seventh compound can be placed in row G1–12.

Samples are made in the following stock concentrations: $10^{-3}$, $10^{-4}$, $10^{-5}$, $10^{-6}$, $10^{-7}$, $10^{-8}$ M in binding buffer. The final concentrations will be one order of magnitude less ($10^{-4}$ to $10^{-9}$). Stock concentration of compounds are usually 25 mM so a 25:1 dilution is required. Make up 6 tubes labeled 4 to −9. Put 100 μl of binding buffer in each tube. Add 4 μl of 25 mM stock to the tube labeled −4. Vortex and take 11 μl of the 4 sample and add to the −5 tube. Repeat until all the dilutions are made. For each row the compound will look like this:

A1,2 −9 (1 nM)
B1,2 −8 (10 nM)
C1,2 −7 (100 nM)
D1,2 −6 (1 μM)
E1,2 −5 (10 μM)
F1,2 −4 (100 μM)

To each well add in order:
20 μl of binding buffer to "total" wells (H1,2).
20 μl of 10 μM AGRP to wells H3,4.
20 μl of 10 μM NDP-MSH to wells H5,6.
170 μl of binding buffer to wells H7,8.
10 μl of 2 nM [$^{125}$I]AGRP to all wells.
170 μl membranes diluted to 5 μg/170 μl in binding buffer to all wells except H7,8.

Procedure:
1. Set up assay for a 96 well filtering system (Unifilter®GF/C™, Packard Instrument Company, Meriden, Conn.).
2. Incubate 90–120 minutes shaking at room temperature.
3. Using a cell harvester, aspirate samples into processing head. Use a pre-soaked (0.3% polyethylene imine) filter.
4. Wash four times with cold wash buffer.
5. Dry plate, add 25 μl of scintillation fluid to each well.
6. Count samples.

Binding Buffer:
50 mM Hepes/10 mM $MgCl_2$, pH 7.4 (made from 10×stock) 0.2% BSA (fraction V)
Protease inhibitors (Made up as 100×stock).
100 μg/ml bacitracin
100 μg/ml benzamidine
5 μg/ml aprotinin
5 μg/ml leupeptin The protease inhibitors can be obtained from Sigma, St. Louis, Mo.

Wash Buffer:
50 mM Hepes/10 mM $MgCl_2$, pH 7.4, ice cold (made from 10×stock).

[$^{125}$I]NDP-MSH Competition Binding Assay

Specific Activity of [$^{125}$I]NDP-MSH is 2200 Ci/mmole. The final concentration of [$^{125}$I]NDP-MSH is 250 pM. Therefore, a 5 nM (20×) stock needs to be made in binding buffer. The concentration of [$^{125}$I]NDP-MSH varies from 40–60 nM. [$^{125}$I]NDP-MSH can be obtained from New England Nuclear, Boston, Mass.

The competition assay can be run using 96 well plates. The last row (Row H) in the 96 well plate should be for total cpm bound (H1,2), 1 μM AGRP (H3,4), 1 μM NDP-MSH (H5,6) and filter blanks (just binding buffer, no membranes; H7,8). The other rows (A–G) should be for compounds to be tested. Up to seven compounds can be tested in 7 point competition curves in a 96 well format. The first six rows for each compound can be used for testing 6 compounds at 6 concentrations in duplicate. An example for a single compound is outlined below. The next compound would be in rows A–F, columns 3 and 4. A seventh compound can be placed in row G1–12.

Samples are made in the following stock concentrations: $10^{-3}$, $10^{-4}$, $10^{-5}$, $10^{-6}$, $10^{-7}$, $10^{-8}$ M in binding buffer. The final concentrations will be one order of magnitude less ($10^{-4}$ to $10^{-9}$). Stock concentration of compounds are usually 25 mM so a 25:1 dilution is required. Make up 6 tubes labeled −4 to −9. Put 100 μl of binding buffer in each tube. Add 4 μl of 25 mM stock to the tube labeled −4. Vortex and take 11 μl of the −4 sample and add to the −5 tube. Repeat until all the dilutions are made. For each row the compound will look like this:

A1,2 −9
B1,2 −8
C1,2 −7
D1,2 −6
E1,2 −5
F1,2 −4

To each well add in order:
20 μl binding buffer to "total" wells (H1,2).
20 μl of 10 μM AGRP to wells H3,4.
20 μl of 10 μM NDP-MSH to wells H5,6.
170 μl of binding buffer to wells H7,8.
10 μl of 2 nM [$^{125}$I]NDP-MSH to all wells.
170 μl membranes diluted to 5 μg/170 μl in binding buffer to all wells except H7,8.

Procedure:
1. Set up assay for a 96 well filtering system (Unifilter® GF/C™, Packard Instrument Company, Meriden, Conn.).
2. Incubate 90–120 minutes shaking at room temperature.
3. Using a cell harvester, aspirate samples into processing head. Use a pre-soaked (0.3% polyethylene imine) filter.

4. Wash four times with cold wash buffer.

5. Dry plate, add 25 µl of scintillation fluid to each well.

6. Count samples.

Binding Buffer:

50 mm hepes/10 mm mgCl$_2$, ph 7.4 (made from 10×stock)

0.2% bsa (fraction v)

protease inhibitors (made up as 10×stock).

100 µg/ml bacitracin

100 µg/ml benzamidine

5 µg/ml aprotinin

5 µg/ml leupeptin

Wash Buffer:

50 mm hepes/10 mm mgCl$_2$, ph 7.4, ice cold (made from 10×stock).

What is claimed is:

1. A method of treating obesity, the method comprising the step of administering to an obese patient a therapeutically effective amount of a compound that attenuates the binding of agouti-related protein to melanocortin receptors, but does not attenuate the binding of α-melanocyte stimulating hormone to melanocortin receptors, wherein the compound is 8,16-bis-(4-nitro-phenyl)-5,6,8,8a,13,14,16,16a-octahydro[1,2,4,5]tetrazino[6,1-a;3,4-a']diisoquinoline.

2. The method of claim 1 wherein the melanocortin receptors are melanocortin-4 or melanocortin-3 receptors.

3. The method of claim 1 wherein the melanocortin receptors are melanocortin-4 receptors.

* * * * *